United States Patent [19]

Weissmüller et al.

[11] Patent Number: 5,097,028

[45] Date of Patent: Mar. 17, 1992

[54] 2-SUBSTITUTED-4-SUBSTITUTED-5-AMINO-2H-PYRIDAZIN-3-ONES

[75] Inventors: Joachim Weissmüller, Monheim; Peter Babczinski, Wuppertal; Klaus Lurssen, Bergisch-Gladbach; Hans-Joachim Santel, Leverkusen; Robert R. Schmidt; Birgit Krauskopf, both of Bergisch-Gladbach, all of Fed. Rep. of Germany

[73] Assignee: Bayer Aktiengesellschaft, Leverkusen, Fed. Rep. of Germany

[21] Appl. No.: 553,497

[22] Filed: Jul. 13, 1990

[30] Foreign Application Priority Data

Jul. 28, 1989 [DE] Fed. Rep. of Germany ....... 3925066
Mar. 27, 1990 [DE] Fed. Rep. of Germany ....... 4009761

[51] Int. Cl.$^5$ .......................................... C07D 237/22
[52] U.S. Cl. .................................... 544/239; 544/241; 71/92
[58] Field of Search ........................... 544/239, 241

[56] References Cited

U.S. PATENT DOCUMENTS

| | | | |
|---|---|---|---|
| 2,798,869 | 7/1957 | Druey et al. | 544/241 |
| 3,210,354 | 10/1965 | Recheneder et al. | 544/241 |
| 3,644,355 | 2/1972 | Ebner | 544/241 |
| 3,967,952 | 2/1976 | Abdulla | 544/239 |
| 4,360,672 | 11/1982 | Parg et al. | 544/241 |
| 4,783,462 | 11/1988 | Mutsukado et al. | 544/239 |
| 4,892,947 | 1/1990 | Mutsukado et al. | 544/239 |
| 4,978,665 | 12/1990 | Tanikawa et al. | 544/239 |

FOREIGN PATENT DOCUMENTS

| | | |
|---|---|---|
| 0193853 | 9/1986 | European Pat. Off. . |
| 0199281 | 10/1986 | European Pat. Off. . |
| 1695840 | 5/1971 | Fed. Rep. of Germany . |
| 0156778 | 6/1988 | Japan ............... 544/241 |

OTHER PUBLICATIONS

Ghozlan et al., Chem. Abstr. vol. 112 entry 20955z (1990).

Karklina et al. Chemical Abstracts, vol. 77, 1972, p. 439.
Gazzetta Chimica Italiana, 119, 1989—Published by Societa Chimica Italiana, pp. 95–97.

*Primary Examiner*—Donald G. Daus
*Attorney, Agent, or Firm*—Sprung, Horn, Kramer & Woods

[57] ABSTRACT

The invention relates to new 2H-pyridazinone derivatives of the general formula (I)

in which $R^1$ represent alkyl, alkoxyalkyl, alkylthioalkyl, aminoalkyl, alkylaminoalkyl, dialkylaminoalkyl, hydroxyalkyl, halogenoalkyl, cyanoalkyl, alkenyl, halogenalkenyl or alkoxycarbonylalkyl, or represents in each case optionally substituted cycloalkyl, cycloalkylalkyl, phenyl or phenylalkyl, $R^2$ represents alkyl, or represents in each case optionally substituted phenyl, phenoxy or phenylalkyl, $R^3$ represents hydrogen, or represents in each case optionally substituted alkyl, cycloalkyl or alkylcarbonyl, and $R^4$ represents hydrogen, hydroxyl, amino, aminocarbonyl (carbamoyl), or represents alkoxy, alkylamino or dialkylamino, or represents in each case optionally substituted alkyl, cycloalkyl, alkylaminocarbonyl, dialkylaminocarbonyl, alkylcarbonyloxy, alkylcarbonylamino, alkylcarbonylalkylamino, bis-(alkylcarbonyl)-amino, alkoxycarbonyl, alkoxycarbonylcarbonyl, formyl or alkylcarbonyl, have been found.

4 Claims, No Drawings

2-SUBSTITUTED-4-SUBSTITUTED-5-AMINO-2H-PYRIDAZIN-3-ONES

The invention relates to new 2H-pyridazinone derivatives, to processes for their preparation, and to their use as herbicides and/or plant growth regulators.

It is known that certain nitrogen-containing heterocycles, such as, for example, 2-(3-trifluoromethylphenyl)-4-chloro-5-methylamino-2H-pyridazin-3-one (cf. DE-OS (German Published Specification) 1,695,840), as well as certain furanones, such as, for example, 5-(methylamino)-2-phenyl-4-[3-(trifluoromethyl-)-phenyl]-2H-furan-3-one (cf. DE-OS (German Published Specification) 3,422,346), have herbicidal properties.

However, the herbicidal activity of these previously known compounds against problem weeds, as well as their tolerance by important crop plants, are not entirely satisfactory in all fields of application.

New 2H-pyridazinone derivatives of the general formula (I)

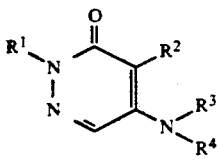

in which

R$^1$ represents alkyl, alkoxyalkyl, alkylthioalkyl, aminoalkyl, alkylaminoalkyl, dialkylaminoalkyl, hydroxyalkyl, halogenoalkyl, cyanoalkyl, alkenyl, halogenoalkenyl or alkoxycarbonylalkyl, or represents in each case optionally substituted cycloalkyl, cycloalkylalkyl, phenyl or phenylalkyl, R$^2$ represents alkyl, or represents in each case optionally substituted phenyl, phenoxy or phenylalkyl, R$^3$ represents hydrogen, or represents in each case optionally substituted alkyl, cycloalkyl or alkylcarbonyl, and R$^4$ represents hydrogen, hydroxyl, amino, aminocarbonyl (carbamoyl), or represents alkoxy, alkylamino or dialkylamino, or represents in each case optionally substituted alkyl, cycloalkyl, alkylaminocarbonyl, dialkylaminocarbonyl, alkylcarbonyloxy, alkylcarbonylamino, alkylcarbonylalkylamino, bis-(alkylcarbonyl)-amino, alkoxycarbonyl, alkoxycarbonylcarbonyl, formyl or alkylcarbonyl, have been found.

It has furthermore been found that the new 2H-pyridazinone derivatives of the general formula (I) are obtained when (a) 2H-5-halogeno-pyridazinone derivatives of the general formula (II)

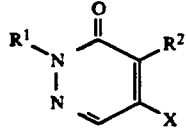

in which

R$^1$ and R$^2$ have the abovementioned meaning and X represents halogen, are reacted with amines of the general formula (III)

in which

R$^3$ and R$^4$ have the abovementioned meaning, if appropriate in the presence of a diluent and if appropriate in the presence of a basic reaction auxiliary (acid-binding agent), or (b) the compounds according to the invention obtained by process (a) of the general formula (Ia)

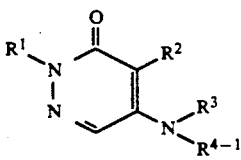

in which

R$^1$, R$^2$ and R$^3$ have the abovementioned meaning, and R$^{4-1}$ represents hydrogen, hydroxyl, amino or alkylamino, are reacted with acylating agents of the general formula (IV)

$$R^{4-2}-Z \qquad (IV)$$

in which

R$^{4-2}$ represents in each case optionally substituted (di)alkylaminocarbonyl, alkoxycarbonyl, alkoxycarbonylcarbonyl or alkylcarbonyl, and Z represents an electron-attracting leaving group, if appropriate in the presence of a diluent and if appropriate in the presence of a basic reaction auxiliary (acid-binding agent).

Finally, it has been found that the new 2H-pyridazinone derivatives of the general formula (I) have herbicidal and growth-regulating properties.

Surprisingly, the 2H-pyridazinone derivatives of the general formula (I) according to the invention have a considerably more powerful herbicidal potency against problem weeds than 5-methylamino-2-phenyl-4-[3-(trifluoromethyl)-phenyl]-2H-furan-3-one, which is known from the prior art, has a related structure and is also similar with regard to its action. The growth-regulating action of some 2H-pyridazinone derivatives of the formula (I) according to the invention is new and surprising.

Formula (I) provides a general definition of the 2H-pyridazinone derivatives according to the invention. Preferred compounds of the formula (I) are those in which R$^1$ represents straight-chain or branched alkyl having 1 to 6 carbon atoms, straight-chain or branched alkoxyalkyl or alkylthioalkyl having in each case 1 to 4 carbon atoms in the alkyl and alkoxy or alkylthio moieties, straight-chain or branched aminoalkyl, alkylaminoalkyl, dialkylaminoalkyl, hydroxyalkyl, halogenoalkyl or cyanoalkyl having in each case 1 to 4 carbon atoms in the respective alkyl moieties and 1–4 halogen atoms in the halogenoalkyl moiety, straight-chain or branched alkenyl or halogenoalkenyl, each of which has 2–6 carbon atoms in the alkenyl moiety and 1–4 halogen atoms in the halogenoalkenyl moiety, straight-chain or branched alkoxycarbonylalkyl having in each case 1–4 carbon atoms in the alkoxy and alkyl moieties, cycloalkyl or cycloalkylalkyl, each of which has 3–6 carbon atoms in the cycloalkyl moiety and where appropriate 1–3 carbon atoms in the straight-chain or branched alkyl moiety and each of which is optionally monosubstituted to tetrasubstituted in the cycloalkyl moiety by identical or different substituents (suitable substituents in each case being: halogen, in each case straight-chain or branched alkyl, alkoxy, halogenoalkyl or halogenoalkoxy, each of which has 1 to 4 carbon atoms and where appropriate 1 to 9 identical or different halogen atoms); or $R^1$ represents phenyl or phenylalkyl, where appropriate having 1–3 carbon atoms in the straight-chain or branched alkyl moiety, each of which is optionally monosubstituted to trisubstituted in the phenyl moiety by identical or different substituents (suitable substituents in each case being: halogen, cyano, nitro, in each case straight-chain or branched alkyl or alkoxy, each of which has 1–6 carbon atoms, or halogenoalkyl or halogenoalkoxy, each of which has 1 or 2 carbon atoms and 1–5 identical or different halogen atoms);

$R^2$ represents straight-chain or branched alkyl having 1–6 carbon atoms, or represents phenyl, phenoxy or phenylalkyl, where appropriate having 1–3 carbon atoms in the straight-chain or branched alkyl moiety, each of which is optionally monosubstituted to trisubstituted in the phenyl moiety by identical or different substituents (suitable substituents in each case being: halogen, cyano, nitro, in each case straight-chain or branched alkyl or alkoxy, each of which has 1–6 carbon atoms, in each case straight-chain or branched halogenoalkyl or halogenoalkoxy, each of which has 1–2 carbon atoms and 1–5 identical or different halogen atoms);

$R^3$ represents hydrogen, or represents in each case straight-chain or branched alkyl having 1–4 carbon atoms (which is optionally substituted by 1–9 identical or different halogen atoms and/or by alkoxy having 1–4 carbon atoms), or represents cycloalkyl which has 3–6 carbon atoms and is optionally monosubstituted to tetrasubstituted by identical or different substituents (suitable substituents in each case being: halogen, and in each case straight-chain or branched alkyl, alkoxy, halogenoalkyl or halogenoalkoxy, each of which has 1–4 carbon atoms and where appropriate 1–9 identical or different halogen atoms) or represents straight-chain or branched and optionally substituted alkylcarbonyl having 1–4 carbon atoms in the alkyl moiety (suitable substituents being 1–3 identical or different halogen atoms), and $R^4$ represents hydrogen, hydroxyl, amino, aminocarbonyl, or represents in each case straight-chain or branched alkoxy, alkylamino or dialkylamino having 1–4 carbon atoms in the respective alkyl moieties or represents in each case straight-chain or branched alkyl having 1–4 carbon atoms (which is optionally substituted by 1–9 identical or different halogen atoms and/or hydroxyl groups or by alkoxy having 1–4 carbon atoms), or represents cycloalkyl which has 3–6 carbon atoms and is optionally monosubstituted to tetrasubstituted by identical or different substituents (suitable substituents in each case being: halogen, and in each case straight-chain or branched alkyl, alkoxy, halogenoalkyl or halogenoalkoxy, each of which has 1–4 carbon atoms and where appropriate 1–9 identical or different halogen atoms), or represents in each case straight-chain or branched alkylaminocarbonyl or dialkylaminocarbonyl having 1–4 carbon atoms in the respective alkyl moieties, or represents alkylcarbonyloxy, alkylcarbonylamino, alkylcarbonylalkylamino or bis(alkylcarbonyl)-amino having 1–4 carbon atoms in the respective alkyl moieties, each of which is optionally monosubstituted to trisubstituted in the alkylcarbonyl moiety by halogen, or represents in each case straight-chain or branched and optionally substituted alkoxycarbonyl or alkoxycarbonylcarbonyl having 1–4 carbon atoms in the alkyl moiety, or represents straight-chain or branched and optionally substituted alkylcarbonyl having 1–4 carbon atoms in the alkyl moiety (suitable substituents being 1–3 identical or different halogen atoms).

Particularly preferred compounds of the formula (I) are those in which $R^1$ represents methyl, ethyl, n- or i-propyl, n-, i-, s- or t-butyl, methoxymethyl, ethoxymethyl, methoxyethyl or ethoxyethyl, methylthiomethyl, ethylthiomethyl, methylthioethyl, ethylthioethyl, aminomethyl, aminoethyl, methylaminomethyl, methylaminoethyl, dimethylaminomethyl, dimethylaminoethyl, ethylaminomethyl, ethylaminoethyl, diethylaminomethyl, diethylaminoethyl, hydroxymethyl, hydroxyethyl, halogenomethyl containing 1–3 fluorine and/or chlorine atoms, halogenoethyl, n- or i-halogenopropyl, n- or i-halogenobutyl, cyanomethyl, cyanoethyl, allyl, n- or i-butenyl, n- or i-pentenyl, 2-fluoropropen-3-yl, 2-chloropropen-3-yl, 1-chloropropen-3-yl, 1,1-dichloropropen-3-yl, 1-fluoropropen-3-yl, 1,1-difluoropropen-3-yl, 1,2-dichloropropen-3-yl, 1,2-difluoropropen-3-yl, 1,1,2-trichloropropen-3-yl, or represents methoxycarbonylmethyl, methoxycarbonylethyl, ethoxycarbonylmethyl or ethoxycarbonylethyl, or represents cyclopentyl, cyclohexyl, cyclopropylmethyl, cyclopentylmethyl, cyclopentylethyl, cyclohexylmethyl or cyclohexylethyl, each of which is optionally monosubstituted to tetrasubstituted in the cycloalkyl moiety by identical or different substituents (suitable substituents in each case being: fluorine, chlorine, bromine, methyl, ethyl, methoxy, ethoxy, halogenomethyl halogenoethyl, halogenomethoxy or halogenoethoxy, halogen preferably representing fluorine and/or chlorine); $R^1$ furthermore represents phenyl, benzyl or phenethyl, each of which is optionally monosubstituted or disubstituted in the phenyl moiety by identical or different substituents (suitable substituents in each case being: fluorine, chlorine, bromine, cyano, nitro, methyl, ethyl, n- or i-propyl, n-, i-, s- or t-butyl, methoxy, ethoxy, trifluoromethyl, difluoromethyl and trifluoromethoxy);

$R^2$ represents methyl, ethyl, n- or i-propyl, n-, i-, s- or t-butyl, or represents phenyl, phenoxy, benzyl or phenethyl, each of which is optionally monosubstituted to disubstituted in the phenyl moiety by identical or different substituents (suitable substituents in each case being: fluorine, chlorine, bromine, cyano, nitro, methyl, ethyl, n- or i-propyl, n-, i-, s- or t-butyl, methoxy, ethoxy, trifluoromethyl, difluoromethyl and trifluoromethoxy);

$R^3$ represents hydrogen, methyl, ethyl, n- or i-propyl, halogenomethyl or halogenoethyl (halogen preferably representing fluorine and/or chlorine), methoxymethyl, methoxyethyl, ethoxymethyl, ethoxyethyl, or represents cyclopropyl which is optionally monosubstituted or disubstituted by identical or different substituents (suitable substituents in each case being: fluorine, chlorine, bromine, methyl and ethyl) or represents acetyl, formyl, propionyl, trifluoroacetyl, trichloroacetyl or chloroacetyl, and R⁴ represents hydrogen, hydroxyl, amino, methoxy, ethoxy, methylamino, ethylamino, dimethylamino, diethylamino, methyl, ethyl, n- or i-propyl, hydroxymethyl, hydroxyethyl, methylaminocarbonyl, ethylaminocarbonyl, dimethylaminocarbonyl, methylethylaminocarbonyl or diethylaminocarbonyl, acetyloxy, trifluoroacetyloxy, acetylamino, trifluoroacetylamino, acetylmethylamino, trifluoroacetylmethylamino, diacetylamino, ditrifluoroacetylamino, methoxycarbonyl, ethoxycarbonyl, methoxycarbonylcarbonyl, ethoxycarbonylcarbonyl, formyl, acetyl, propionyl, difluoroacetyl, trifluoroacetyl, chloroacetyl, dichloroacetyl or trichloroacetyl.

Very particularly preferred compounds of the formula (I) are those in which $R^1$ represents methyl, ethyl, n- or i-propyl, n-, i-, s- or t-butyl, methoxymethyl, ethoxymethyl, methoxyethyl, methylthiomethyl, ethylthiomethyl, methylthioethyl, dimethylaminomethyl, hydroxymethyl, 1,1,1-trifluoroethyl, allyl, n- or i-butenyl, n- or i-pentenyl, 2-fluoropropen-3-yl, 2-chloropropen-3-yl, 1-chloropropen-3-yl, 1,1-dichloropropen-3-yl, 1-fluoropropen-3-yl, 1,1-difluoropropen-3-yl, 1,2-dichloropropen-3-yl, 1,2-difluoropropen-3-yl1,2-trichloropropen-3-yl, cyclopropylmethyl, 1,1-dichlorocyclopropylmethyl, 1,1-difluorocyclopropylmethyl, 1,1-dimethylcyclopropylmethyl-, 1,1-dimethyl-2,2-dichlorocyclopropylmethyl, or represents cyclopentyl or cyclohexyl, each of which is optionally monosubstituted or disubstituted (suitable substituents being methyl and/or ethyl), or represents phenyl which is optionally monosubstituted or disubstituted by identical or different substituents (suitable substituents being: fluorine, chlorine, bromine, methyl, ethyl, methoxy, ethoxy, trifluoromethyl or trifluoromethoxy);

$R^2$ represents methyl, ethyl, n- or i-propyl, n-, i-, s- or t-butyl, or represents phenyl which is monosubstituted or disubstituted, suitable substituents being: fluorine, chlorine, bromine, methyl, ethyl, methoxy, ethoxy, trifluoromethyl or trifluoromethoxy, $R^3$ represents hydrogen, methyl, ethyl or n- or i-propyl, acetyl or trifluoroacetyl, and $R^4$ represents hydroxyl, amino, methylamino, dimethylamino, methyl, ethyl, n- or i-propyl, acetyloxy, trifluoroacetyloxy, acetylamino, trifluroacetylamino, acetylmethylamino, trifluoroacetylmethylamino, diacetylamino, ditrifluoroacetylamino, acetyl or trifluoroacetyl.

The following 2H-pyridazinone derivatives of the general formula (I) may be mentioned individually in addition to the compounds mentioned in the Preparation Examples:

TABLE 1

(I)

| $R^1$ | $R^2$ | $R^3$ | $R^4$ |
|---|---|---|---|
| 3-CF₃-phenyl | phenyl | H | —COCH₃ |
| 3-CF₃-phenyl | phenyl | H | —CH₂—CH₂—OCH₃ |
| 3-CF₃-phenyl | 4-F-phenyl | H | —CH₃ |
| 3-CF₃-phenyl | 2-Cl-phenyl | H | —CH₃ |
| 3-CF₃-phenyl | 3-CH₃-phenyl | —CO—CH₃ | —CH₃ |

TABLE 1-continued $$\text{(I)}$$

Structure: Pyridazinone of formula (I) with R¹ on N, R² at 3-position, and NR³R⁴ at 4-position.

| R¹ | R² | R³ | R⁴ |
|---|---|---|---|
| 3-CF₃-phenyl | 3-CH₃-phenyl | CH₃ | —CO—CF₃ |
| 3-CF₃-phenyl | 3-CH₃-phenyl | H | —NHCH₃ |
| 3-CF₃-phenyl | 3-CH₃-phenyl | H | —N(CH₃)—CO—CH₃ |
| 3-CF₃-phenyl | 3-CH₃-phenyl | H | —OH |
| 3-CF₃-phenyl | 3-CH₃-phenyl | —CO—CH₃ | —O—CO—CH₃ |
| 3-CF₃-phenyl | 3-Cl-phenyl | H | —CH₃ |
| 3-CF₃-phenyl | 4-Cl-phenyl | H | —CH₃ |
| phenyl | 3-CF₃-phenyl | H | —CH₃ |
| 2-Cl-phenyl | 3-CF₃-phenyl | H | —CH₃ |

TABLE 1-continued
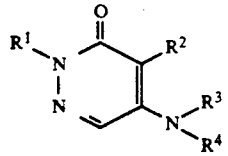

TABLE 1-continued
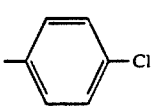
(I)
| R¹ | R² | R³ | R⁴ |
|---|---|---|---|
| —CH₃ | 4-Cl-C₆H₄ | H | —CH₃ |
| —CH₃ | 2-CF₃-C₆H₄ | H | —CH₃ |
| —CH₃ | 3-CF₃-C₆H₄ | H | —CH₃ |
| —CH₃ | 4-CF₃-C₆H₄ | H | —CH₃ |
| —CH₂CH₂CH₃ | 2-Cl-C₆H₄ | H | —CH₃ |
| —CH₂CH₂CH₃ | 4-Cl-C₆H₄ | H | —CH₃ |
| —CH₂CH₂CH₃ | 2-CF₃-C₆H₄ | H | —CH₃ |
| —CH₂CH₂CH₃ | 3-CF₃-C₆H₄ | H | —CH₃ |
| —CH₂CH₂CH₃ | 4-CF₃-C₆H₄ | H | —CH₃ |
| —CH₂CH₂CH₃ | 3-Cl-C₆H₄ | H | —CH₃ |

TABLE 1-continued
(I)
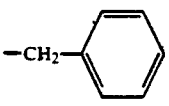
| R¹ | R² | R³ | R⁴ |
|---|---|---|---|
| -CH₂-C₆H₅ | 2-Cl-C₆H₄- | H | -CH₃ |
| -CH₂-C₆H₅ | 3-Cl-C₆H₄- | H | -CH₃ |
| -CH₂-C₆H₅ | 4-Cl-C₆H₄- | H | -CH₃ |
| -CH₂-C₆H₅ | 2-CF₃-C₆H₄- | H | -CH₃ |
| -CH₂-C₆H₅ | 3-CF₃-C₆H₄- | H | -CH₃ |
| -CH₂-C₆H₅ | 4-CF₃-C₆H₄- | H | -CH₃ |
| 3-CF₃-C₆H₄- | -CH₂CH₂CH₃ | H | -CH₃ |
| 3-CF₃-C₆H₄- | -CH₃ | H | -CH₃ |
| 3-CF₃-C₆H₄- | -CH₂-C₆H₅ | H | -CH₃ |
| 3-CF₃-C₆H₄- | 3-CF₃-C₆H₄- | H | -CH₂CH₂OH |

TABLE 1-continued (I)

$$\text{structure with } R^1\text{-N, N, R}^2, R^3, R^4$$

| R¹ | R² | R³ | R⁴ |
|---|---|---|---|
| phenyl | 3-CF₃-phenyl | H | —COCH₃ |
| phenyl | 3-CF₃-phenyl | H | —COCF₃ |
| phenyl | 3-CF₃-phenyl | H | —CO—COOC₂H₅ |
| —CH₃ | 3-CF₃-phenyl | H | —COCH₃ |
| —CH₂CH₂CH₃ | 3-CF₃-phenyl | H | —COCH₃ |
| —CH₂-phenyl | 3-CF₃-phenyl | H | —COCH₃ |
| H | 3-CF₃-phenyl | H | —CH₃ |
| —CH₂—CH=CH₂ | 3-CF₃-phenyl | CH₃ | —COCH₃ |
| —CH₂—CH=CH₂ | 3-CF₃-phenyl | CH₃ | —COCF₃ |

TABLE 1-continued
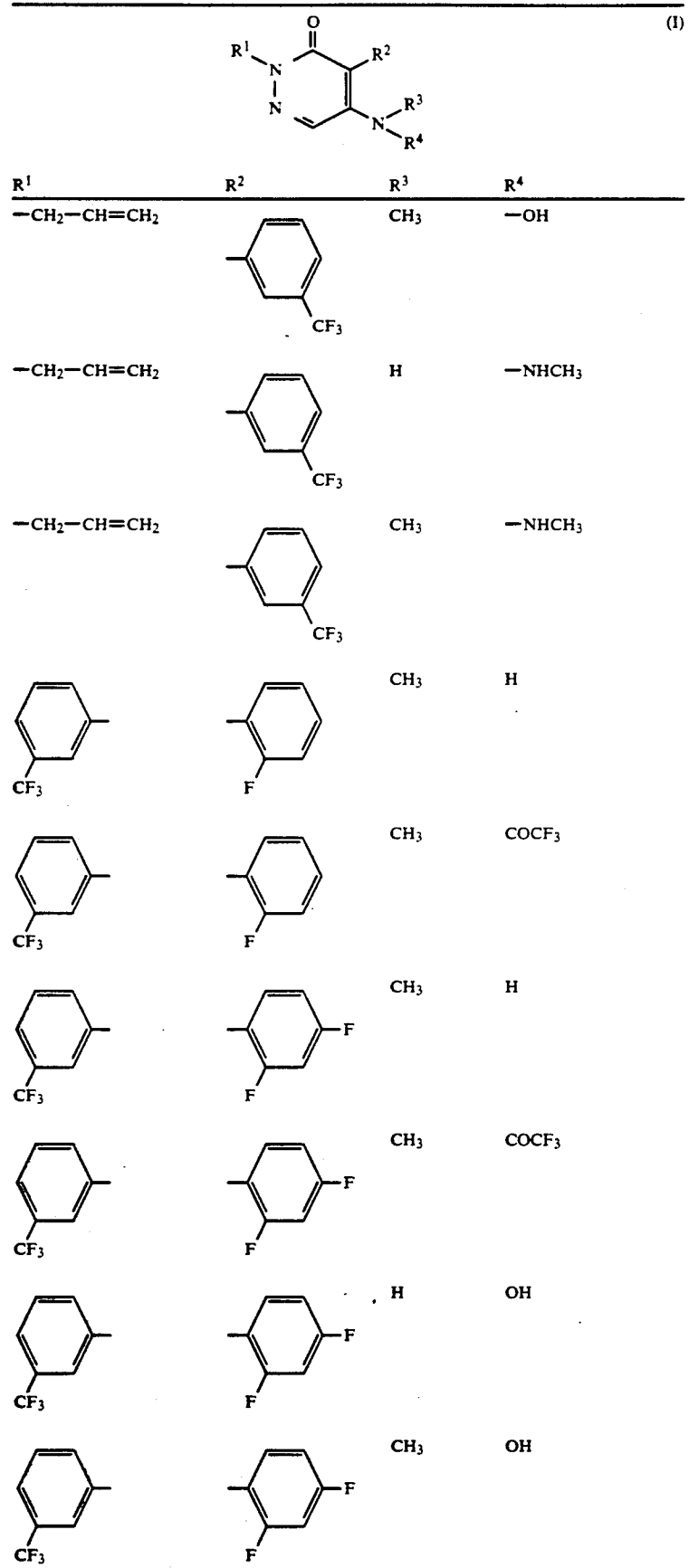
| R¹ | R² | R³ | R⁴ |
|---|---|---|---|
| —CH₂—CH=CH₂ | 3-CF₃-C₆H₄ | CH₃ | —OH |
| —CH₂—CH=CH₂ | 3-CF₃-C₆H₄ | H | —NHCH₃ |
| —CH₂—CH=CH₂ | 3-CF₃-C₆H₄ | CH₃ | —NHCH₃ |
| 3-CF₃-C₆H₄ | 2-F-C₆H₄ | CH₃ | H |
| 3-CF₃-C₆H₄ | 2-F-C₆H₄ | CH₃ | COCF₃ |
| 3-CF₃-C₆H₄ | 2,4-F₂-C₆H₃ | CH₃ | H |
| 3-CF₃-C₆H₄ | 2,4-F₂-C₆H₃ | CH₃ | COCF₃ |
| 3-CF₃-C₆H₄ | 2,4-F₂-C₆H₃ | H | OH |
| 3-CF₃-C₆H₄ | 2,4-F₂-C₆H₃ | CH₃ | OH |

TABLE 1-continued $$\text{(I)}$$

Structure: pyridazinone with R¹ on N1, C=O, R² at C4, NR³R⁴ at C5.

| R¹ | R² | R³ | R⁴ |
|---|---|---|---|
| 3-CF₃-phenyl | 2,4-difluorophenyl | H | NHCH₃ |
| 3-CF₃-phenyl | 2,4-difluorophenyl | CH₃ | NH₂ |
| 3-CF₃-phenyl | 2,4-difluorophenyl | CH₃ | NHCH₃ |
| —CH₂—CH=CHCH₃ | 3-CF₃-phenyl | CH₃ | H |
| —CH₂—CH=CHCH₃ | 3-CF₃-phenyl | CH₃ | —NHCH₃ |
| —CH₂—CH=CHCH₃ | 3-CF₃-phenyl | CH₃ | —COCF₃ |
| —CH₂—CH=CHCH₃ | 3-CF₃-phenyl | H | OH |
| —CH₂—CH=CHCH₃ | 3-CF₃-phenyl | CH₃ | OH |
| —CH₂—CH=C(CH₃)₂ | 3-CF₃-phenyl | CH₃ | H |

TABLE 1-continued
$$\text{(I)}$$
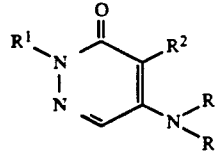
| R¹ | R² | R³ | R⁴ |
|---|---|---|---|
| —CH₂—CH=C(CH₃)₂ | 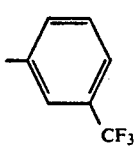 | CH₃ | COCF₃ |
| 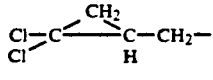 | 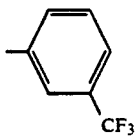 | CH₃ | —NH₂ |
| 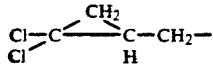 | 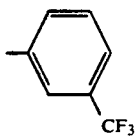 | CH₃ | —NHCH₃ |
| 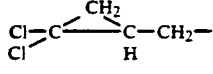 | 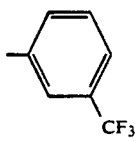 | H | —N(CH₃)₂ |
| 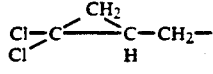 | 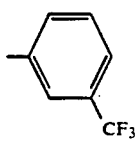 | COCF₃ | —N(CH₃)(CO—CF₃) |
| 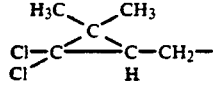 | 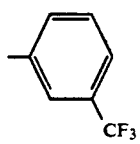 | H | CH₃ |
| 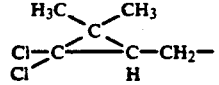 | 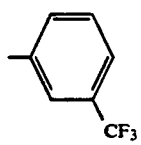 | CH₃ | NH₂ |
| 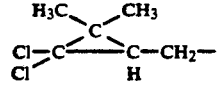 | 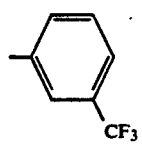 | CH₃ | NHCH₃ |
| 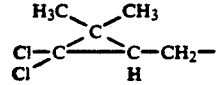 | 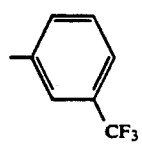 | —COCF₃ | —N(CH₃)(COCF₃) |

TABLE 1-continued
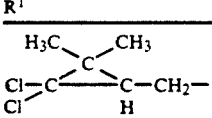
| R¹ | R² | R³ | R⁴ |
|---|---|---|---|
| 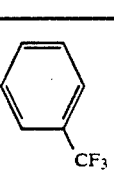 | 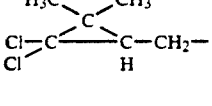 | H | —OH |
| 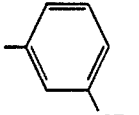 | 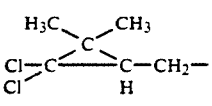 | CH₃ | —OH |
| 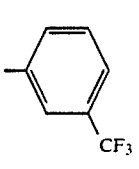 | 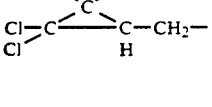 | CH₃ | —OCOCF₃ |
| 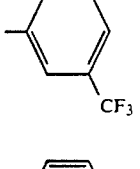 | 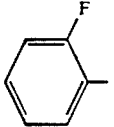 | CH₃ | —COCF₃ |
| 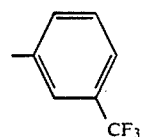 | 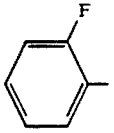 | H | CH₃ |
| 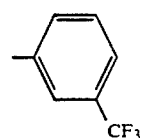 | 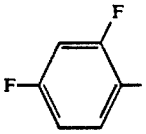 | COCF₃ | CH₃ |
| 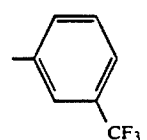 | 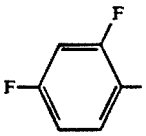 | H | CH₃ |
| 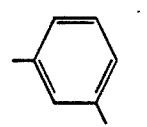 | 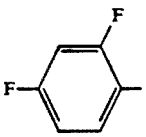 | H | OH |
| 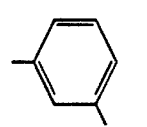 |  | CH₃ | OH |

TABLE 1-continued
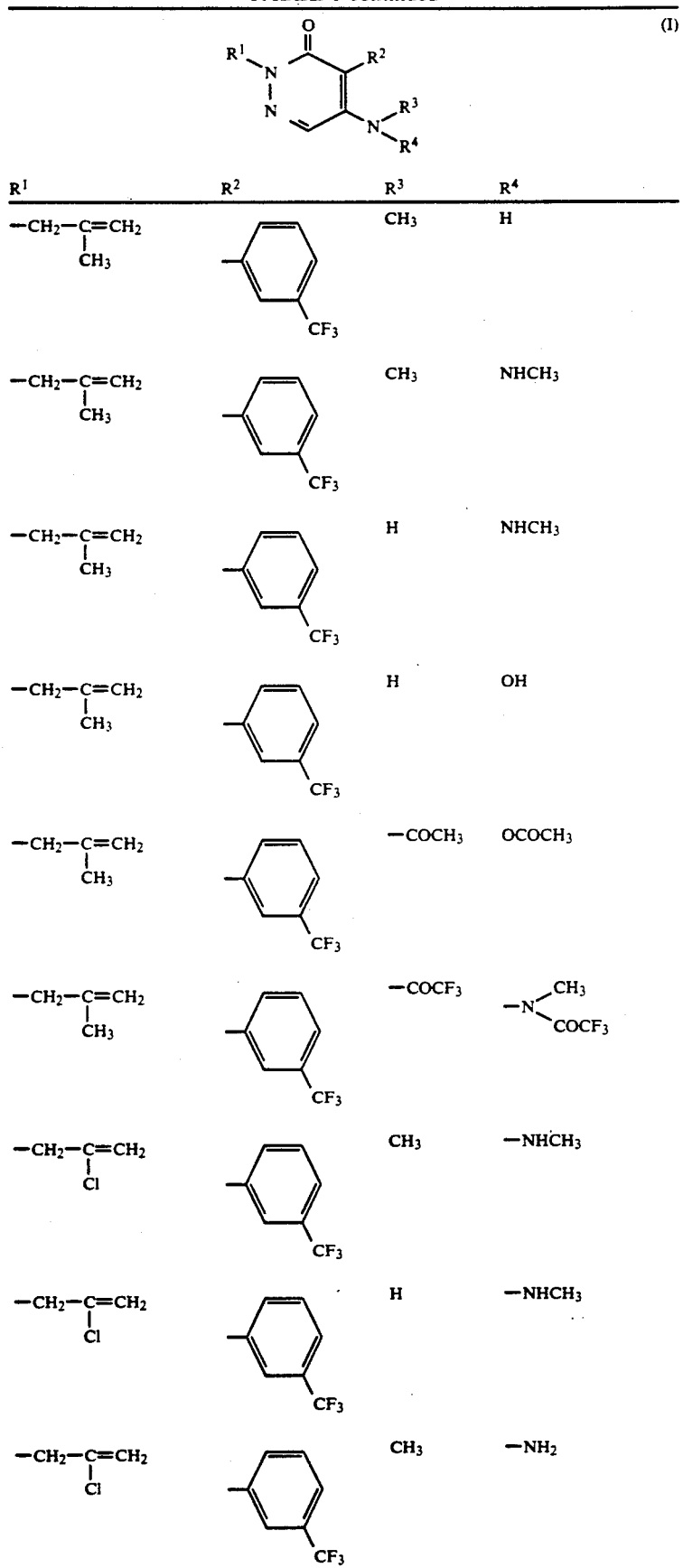
(I)
| R¹ | R² | R³ | R⁴ |
|---|---|---|---|
| −CH₂−C(CH₃)=CH₂ | 3-CF₃-phenyl | CH₃ | H |
| −CH₂−C(CH₃)=CH₂ | 3-CF₃-phenyl | CH₃ | NHCH₃ |
| −CH₂−C(CH₃)=CH₂ | 3-CF₃-phenyl | H | NHCH₃ |
| −CH₂−C(CH₃)=CH₂ | 3-CF₃-phenyl | H | OH |
| −CH₂−C(CH₃)=CH₂ | 3-CF₃-phenyl | −COCH₃ | OCOCH₃ |
| −CH₂−C(CH₃)=CH₂ | 3-CF₃-phenyl | −COCF₃ | −N(CH₃)(COCF₃) |
| −CH₂−C(Cl)=CH₂ | 3-CF₃-phenyl | CH₃ | −NHCH₃ |
| −CH₂−C(Cl)=CH₂ | 3-CF₃-phenyl | H | −NHCH₃ |
| −CH₂−C(Cl)=CH₂ | 3-CF₃-phenyl | CH₃ | −NH₂ |

TABLE 1-continued
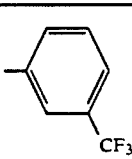
(I)
| R¹ | R² | R³ | R⁴ |
|---|---|---|---|
| −CH₂−C(Cl)=CH₂ | 3-CF₃-C₆H₄− | CH₃ | −COCH₃ |
| −CH₂−C(Cl)=CH₂ | 3-CF₃-C₆H₄− | H | −OH |
| −CH₂−CH=C(Cl₂) | 3-CF₃-C₆H₄− | CH₃ | −OH |
| −CH₂−CH=C(Cl₂) | 3-CF₃-C₆H₄− | CH₃ | −H |
| −CH₂−CH=C(Cl₂) | 3-CF₃-C₆H₄− | CH₃ | −NHCH₃ |
| −CH₂−CH=C(Cl₂) | 3-CF₃-C₆H₄− | H | −NHCH₃ |
| −CH₂−CH=C(Cl₂) | 3-CF₃-C₆H₄− | −CH₃ | −N(CH₃)CO−CF₃ |
| Cl₂C=CH−CH(−)−CH₂− | 3-CF₃-C₆H₄− | CH₃ | −N(CH₃)CO−CF₃ |
| Cl₂C=CH−CH(−)−CH₂− | 3-CF₃-C₆H₄− | CH₃ | −OH |

TABLE 1-continued (I)

$$\text{structure with } R^1\text{-N, N, R}^2, \text{=O, NR}^3R^4$$

| R¹ | R² | R³ | R⁴ |
|---|---|---|---|
| CH₃OCH₂— | 3-CF₃-C₆H₄— | CH₃ | H |
| CH₃OCH₂— | 3-CF₃-C₆H₄— | CH₃ | —COCF₃ |
| CH₃OCH₂— | 3-CF₃-C₆H₄— | H | NHCH₃ |
| CH₃OCH₂— | 3-CF₃-C₆H₄— | H | OH |
| CH₃OCH₂— | 3-CF₃-C₆H₄— | CH₃ | OH |
| (CH₃)₂N—CH₂— | 3-CF₃-C₆H₄— | CH₃ | H |
| (CH₃)₂N—CH₂— | 3-CF₃-C₆H₄— | CH₃ | COCF₃ |
| (CH₃)₂N—CH₂— | 4-CF₃-C₆H₄— | CH₃ | NHCH₃ |
| (CH₃)₂N—CH₂— | 4-CF₃-C₆H₄— | H | OH |

TABLE 1-continued (I)

structure: R¹-N-N=CH-... pyridazinone with R², NR³R⁴

| R¹ | R² | R³ | R⁴ |
|---|---|---|---|
| (H₃C)₂N—CH₂— | 3-CF₃-phenyl | CH₃ | OH |
| 3-NO₂-phenyl | 3-CF₃-phenyl | CH₃ | H |
| 3-NO₂-phenyl | 3-CF₃-phenyl | H | NHCH₃ |
| 3-NO₂-phenyl | 3-CF₃-phenyl | H | OH |
| 3-NO₂-phenyl | 3-CF₃-phenyl | CH₃ | OH |

If, for example, 2-[4-fluorophenyl]-4-[3-trifluoromethylphenyl]-5-chloro-2H-pyridazin-3-one and methylamine are used as starting substances, the course of the reaction of process (a) according to the invention may be represented by the following equation:

If, for example, 2-[4-fluorophenyl]-4-[3-trifluoromethylphenyl]-5-methylamino-2H-pyridazin-3-one, prepared by process (a), and acetyl chloride are used as starting substances, the course of the reaction of process (b) according to the invention may be represented by the following equation:

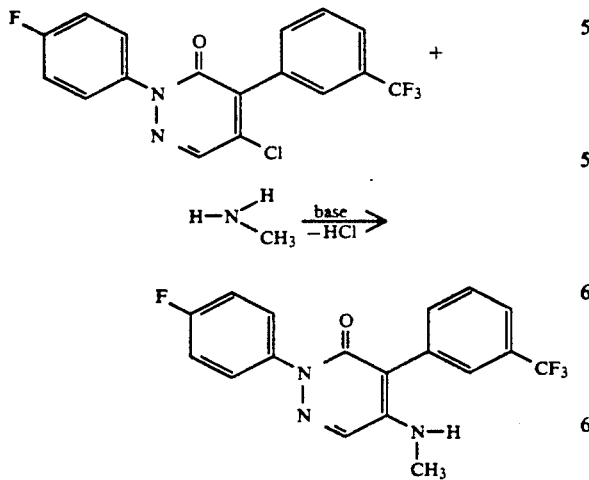

-continued

[Chemical structure: 4-fluorophenyl-N-N= ring with C=O, connected to phenyl-CF3 and N(CH3)-COCH3 substituents]

Formula (II) provides a general definition of the 2H-5-halogeno-pyridazinone derivatives to be used as starting substances in process (a) according to the invention for the preparation of compounds of the formula (I).

$R^1$ and $R^2$ in formula (II) preferably, or in particular, have the meanings which have already been mentioned above as being preferred, or particularly preferred, for $R^1$ and $R^2$ in connection with the description of the compounds of the formula (I) according to the invention.

X represents halogen in formula (II), preferably chlorine or bromine, in particular chlorine.

The 2H-5-halogeno-pyridazinone derivatives of the formula (II) are known in some cases and/or can be prepared by processes known per se (cf., for example, EP 199,281, EP 193,853; Latv. PSR Zinat. Akad. Vestis. Kim. Ser., (4), p. 496–497 (1972)).

Hitherto unknown were 2H-5-halogeno-pyridazinone derivatives of the general formula (IIa)

[Chemical structure IIa]

in which $R^{1-1}$ represents alkyl, alkoxyalkyl, alkylthioalkyl, aminoalkyl, (di)alkylaminoalkyl, hydroxyalkyl, halogenoalkyl, alkenyl, halogenoalkenyl, or represents in each case optionally substituted cycloalkyl, cycloalkylalkyl, phenyl or phenylalkyl;

$R^{2-1}$ represents in each case optionally substituted phenyl or phenylalkyl, and X represents halogen.

Preferred compounds of the formula (IIa) are those in which $R^{1-1}$ represents in each case straight-chain or branched alkyl, alkoxyalkyl and (di)alkylaminoalkyl having 1 to 4 carbon atoms in the respective alkyl moieties, or represents cyclopentyl or cyclohexyl, each of which is optionally monosubstituted to trisubstituted by identical or different substituents, suitable substituents being methyl or halogen, or represents cyclopropylmethyl which is optionally monosubstituted to tetrasubstituted by identical or different substituents, suitable substituents being methyl or halogen, or represents alkenyl having 2–6 carbon atoms, which is optionally substituted by one to four halogen atoms or represents phenyl or phenylalkyl, where appropriate having 1 to 3 carbon atoms in the straight-chain or branched alkyl moiety, each of which is optionally monosubstituted to trisubstituted in the phenyl moiety by identical or different substituents, suitable substituents in each case being: halogen, cyano, nitro, in each case straight-chain or branched alkyl or alkoxy, each of which has 1 to 6 carbon atoms, or halogenoalkyl or halogenoalkoxy, each of which has 1 or 2 carbon atoms and 1 to 5 identical or different halogen atoms;

$R^{2-1}$ represents phenyl or phenylalkyl, where appropriate having 1–3 carbon atoms in the straight-chain or branched alkyl moiety, each of which is optionally monosubstituted to trisubstituted in the phenyl moiety by identical or different substituents, suitable substituents in each case being: halogen, cyano, nitro, in each case straight-chain or branched alkyl or alkoxy, each of which has 1–6 carbon atoms, or halogenoalkyl or halogenoalkoxy, each of which has 1 or 2 carbon atoms and 1 to 5 identical or different halogen atoms, and X represents chlorine or bromine.

Particularly preferred compounds of the formula (IIa) are those in which $R^{1-1}$ represents methyl, ethyl, n- or i-propyl, n-, i-, s- or t-butyl, methoxymethyl, ethoxymethyl, methoxyethyl, dimethylaminomethyl, allyl, n- or i-butenyl, n- or i-pentenyl, 2-fluoropropen-3-yl, 2-chloropropen-3-yl, 1-chloropropen-3-yl, 1,1-dichloropropen-3-yl, 1-fluoropropen-3-yl, 1,1-difluoropropen- 3-yl, 1,2-dichloropropen-3-yl, 1,2-difluoropropen-3-yl, 1,1,2-trichloropropen-3-yl, cyclopropylmethyl, 1,1-dichlorocyclopropylmethyl, 1,1-difluorocyclopropylmethyl, 1,1-dimethylcyclopropylmethyl, 1,1-dimethyl-2,2-dichlorocyclopropylmethyl, or represents cyclopentyl or cyclohexyl, each of which is optionally monosubstituted or disubstituted, suitable substituents being methyl and/or ethyl, or represents phenyl which is optionally monosubstituted or disubstituted by identical or different substituents, suitable substituents being: fluorine, chlorine, bromine, methyl, ethyl, methoxy, ethoxy, trifluoromethyl or trifluoromethoxy, $R^{2-1}$ represents phenyl which is optionally monosubstituted or disubstituted by identical or different substituents, suitable substituents being: fluorine, chlorine, bromine, methyl, ethyl, methoxy, ethoxy, trifluoromethyl or trifluoromethoxy, and X represents chlorine.

These new compounds of the formula (IIa)

[Chemical structure IIa]

in which $R^{1-1}$, $R^{2-1}$ and X have the meanings mentioned above for formula (IIa),
are obtained when, in a first reaction step, hydrazine derivatives of the formula (V)

$$R^{1-1}-NH-NH_2 \quad (V)$$

in which $R^{1-1}$ has the abovementioned meaning, are reacted with mucohalic acids of the formula (VI)

[Chemical structure VI: X-C(COOH)=C(X)-CHO]

in which $X^1$ represents halogen, if appropriate in the presence of a diluent such as, for example, methanol, ethanol, toluene or acetic acid, at temperatures between 0° C. and 150° C., preferably between 20° C. and 110° C., (cf. also Angew. Chem. 77, 282 (1965)) and, in a second reaction step, the resulting 4,5-dihalogenopyridazinone derivatives of the formula (VII)

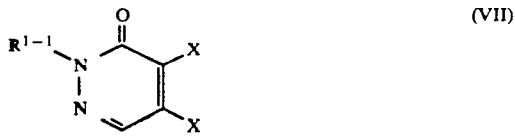

in which
R$^{1-1}$ has the abovementioned meaning and
X represents halogen,
are reacted with Grignard compounds of the general formula (VIII)

in which
R$^{2-1}$ has the abovementioned meaning and
X$^1$ represents halogen, in particular chlorine or bromine,
if appropriate in the presence of a diluent such as, for example, diethyl ether or tetrahydrofuran, at temperatures between 0° C. and 150° C., preferably between 20° C. and 80° C.

In the case of functional groups (hydroxyl, amino) in the substituent R$^{1-1}$, these should be protected in a conventional manner by protective groups, if appropriate before carrying out the Grignard reaction.

Hydrazine derivatives of the formula (V), mucohalic acids of the formula (VI) and Grignard compounds of the formula (VIII) are generally known compounds of organic chemistry and can be obtained in a generally known manner.

The compounds of the formula (VII) produced as intermediates are known or can be prepared by known methods, including for example by alkylating the corresponding unsubstituted 4,5-dihalogeno-3(2H)-pyridazinone derivatives of the formula (VII) (cf. for example Monatshefte für Chemie 99, 15–84 (1968), Synth. Commun. 1981, 631).

Formula (III) provides a general definition of the amines furthermore to be used as starting substances in process (a) according to the invention for the preparation of compounds of the formula (I).

R$^3$ and R$^4$ in formula (III) preferably, or in particular, have those meanings which have already been mentioned above as being preferred, or particularly preferred, for R$^3$ and R$^4$ in connection with the description of the compounds of the formula (I) according to the invention.

Amines of the formula (III) are compounds generally known in organic chemistry.

Formula (Ia) provides a general definition of the 2H-pyridazinone derivatives to be used as starting substances in process (b) according to the invention for the preparation of compounds of the formula (I).

R$^1$, R$^2$ and R$^3$ in formula (Ia) preferably, or in particular, have those meanings which have already been mentioned above as being preferred, or particularly preferred, for R$^1$, R$^2$ and R$^3$, in connection with the description of the compounds of the formula (I) according to the invention. R$^{4-1}$ preferably represents hydrogen, hydroxyl or amino, or represents C$_1$-C$_4$-alkylamino (in particular methylamino).

2H-pyridazinone derivatives of the formula (Ia) are compounds according to the invention.

Formula (IV) provides a general definition of the acylating agents to be used as starting substances in process (b) according to the invention for the preparation of compounds of the formula (I).

In formula (IV),
R$^{4-2}$ preferably represents straight-chain or branched (di)alkylaminocarbonyl having 1–4 carbon atoms in the respective alkyl moieties, in each case straight-chain or branched alkoxycarbonyl or alkoxycarbonylcarbonyl having 1–4 carbon atoms in the alkyl moiety, and also represents straight-chain or branched alkylcarbonyl having 1–4 carbon atoms in the alkyl moiety and optionally substituted by 1–3 halogen atoms;

R$^{4-2}$ in particular represents methylaminocarbonyl, dimethylaminocarbonyl, ethylaminocarbonyl, diethylaminocarbonyl or methylethylaminocarbonyl, or represents methoxycarbonyl or ethoxycarbonyl, methoxycarbonylcarbonyl or ethoxycarbonylcarbonyl, and also represents formyl, acetyl, propionyl, trifluoroacetyl, chloroacetyl, dichloroacetyl or trichloroacetyl.

Z in formula (IV) preferably represents halogen, in particular chlorine or bromine.

In a particular embodiment of process (b) according to the invention, it is also possible to employ corresponding carboxylic anhydrides as acylating agents of the formula (IV).

Suitable diluents for carrying out processes (a) and (b) according to the invention are inert organic solvents or aqueous systems. The organic solvents include, in particular, aliphatic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran, ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

Suitable acid-binding agents for carrying out processes (a) and (b) according to the invention are all inorganic and organic bases which can customarily be used. The hydrides, hydroxides, amides, carbonates or hydrogen carbonates of alkali metals, such as, for example, sodium hydride, sodium amide, sodium hydroxide, sodium carbonate or sodium hydrogen carbonate, and also tertiary amines, such as, for example, triethylamine, N,N-dimethylaniline, pyridine, 4-(N,N-dimethylamino)pyridine, diazabicyclooctane (DABCO), diazabicyclononene (DBN) or diazabicycloundecene (DBU), are preferably used.

In process (a) according to the invention, it is also possible to employ the amines of the formula (III), which are used as reactants, in appropriate excess to act simultaneously as acid-binding agents.

When carrying out the processes (a) and (b) according to the invention, the reaction temperatures can be varied within a substantial range. In general, the process is carried out at temperatures between −20° C. and +150°, preferably at temperatures between 0° C. and +120° C.

Processes (a) and (b) according to the invention are customarily carried out under atmospheric pressure. However, it is also possible to carry out the process under increased pressure.

For carrying out process (a) according to the invention, 1.0 to 10.0 moles, preferably 1.0 to 5.0 moles, of amine of the formula (III) and if appropriate 1.0 to 10.0 moles, preferably 1.0 to 5.0 moles, of acid-binding agent are generally employed per mole of 2H TM 5-halogenopyridazinone derivative of the formula (II).

For carrying out process (b) according to the invention, 1.0 to 5.0 moles, preferably 1.0 to 2.0 moles, of acylating agent of the formula (IV), and 1.0 to 5.0 moles, preferably 1.0 to 2.0 moles, of acid-binding agent are generally employed per mole of 2H-pyridazinone derivative of the formula (Ia).

In both cases, the reaction is carried out and the reaction products of the formula (I) are worked up and isolated by customary methods.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used; for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf, meadows and pastures, and for the selective combating of weeds in annual cultures.

In this context, the active compounds according to the invention are particularly suitable for selectively combating dicotyledon and monocotyledon weeds in monocotyledon and dicotyledon crops, using the pre-emergence and post-emergence methods.

The active compounds according to the invention additionally engage in the metabolism of the plants and can therefore also be employed in some cases as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

The amount of leaves on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

For combating weeds, the active compounds according to the invention, as such or in the form of their formulations, can also be used as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl-1,2,4-triazin-5(4H)-one (METAMITRON) for combating weeds in sugar beets, and 4-amino-6-(1,1-dimethylethyl)-3-methylthio-1,2,4-tirazin-5(4H)-one (METRIBUZIN) for combating weeds in soya beans.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.001 and 10 kg of active compound per hectare of soil surface, preferably between 0.005 and 5 kg per ha.

The preparation and use of the active compounds according to the invention can be seen from the following examples.

PREPARATION EXAMPLES

Example 1

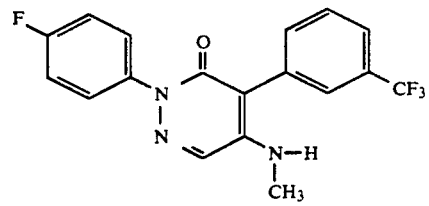

A mixture of 1,4 g (0.0038 mol) of 2-[4-fluorophenyl]-4-[3-trifluoromethylphenyl]-5-chloro-2H-pyridazin-3-one and 1.2 g (0.039 mol) of methylamine (30% strength solution in H₂O) in 50 ml of ethanol is stirred for 16 hours at room temperature. The reaction mixture is subsequently concentrated and the residue is taken up in methylene chloride/water. The organic phase is dried over sodium sulphate, concentrated and chromatographed on silica gel 60 using methylene chloride.

This gives 0.5 g (35% of theory) of 2-[4-fluorophenyl]-4-[3-trifluoromethylphenyl]-5-methylamino-2H-pyridazin-3-one of melting point 161°–162° C.

The following 2H-pyridazinone derivatives of the general formula (I)

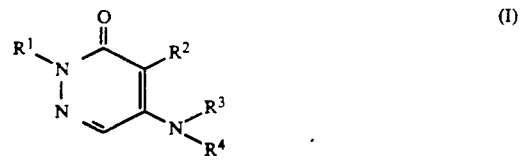

are obtained in a corresponding manner and following the general instructions of processes (a) and (b)

TABLE 2

| Example No. | R¹ | R² | R³ | R⁴ | Melting point or refractive index |
|---|---|---|---|---|---|
| 2 | ⌬–F | ⌬ | H | —CH₃ | 174–175° C. |
| 3 | ⌬ | ⌬ | H | —CH₃ | 156–157° C. |
| 4 | ⌬–Cl | ⌬ | H | —CH₃ | 204–205° C. |

TABLE 2-continued

| Example No. | R¹ | R² | R³ | R⁴ | Melting point or refractive index |
|---|---|---|---|---|---|
| 5 | phenyl | 4-Cl-phenyl | H | —CH₃ | 58–60° C. |
| 6 | phenyl | 3-CF₃-phenyl | H | —CH₃ | 58–60° C. |
| 7 | —CH₃ | 3-CF₃-phenyl | H | —CH₃ | 117–118° C. |
| 8 | 3-CF₃-phenyl | 4-Cl-phenyl | H | —CH₃ | 115° C. |
| 9 | 3-CF₃-phenyl | 3-CF₃-phenyl | H | —CH₃ | 99–100° C. |
| 10 | —CH₂-phenyl | 3-CF₃-phenyl | H | —CH₃ | $n_D^{20} = 1.5838$ |
| 11 | 4-F-phenyl | 4-Cl-phenyl | H | —CH₃ | 177–178° C. |
| 12 | 4-Cl-phenyl | 4-Cl-phenyl | H | —CH₃ | 185–186° C. |
| 13 | —CH₃ | 4-Cl-phenyl | H | —CH₃ | 58–60° C. |
| 14 | —CH₂-phenyl | 4-Cl-phenyl | H | —CH₃ | 84–85° C. |
| 15 | 4-Cl-phenyl | 3-CF₃-phenyl | H | —CH₃ | 75–76° C. |

TABLE 2-continued
| Example No. | R¹ | R² | R³ | R⁴ | Melting point or refractive index |
|---|---|---|---|---|---|
| 16 | 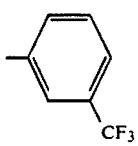 | 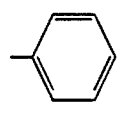 | H | —CH₃ | 147–148° C. |
| 17 | 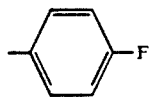 | 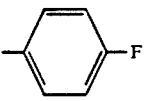 | H | —CH₃ | 81–83° C. |
| 18 | 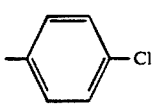 | 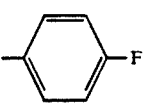 | H | —CH₃ | 81–83° C. |
| 19 | 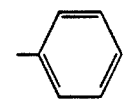 | 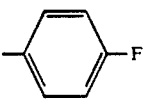 | H | —CH₃ | 62–64° C. |
| 20 | 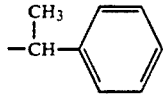 | 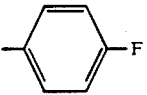 | H | —CH₃ | 138–139° C. |
| 21 | 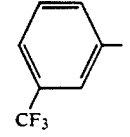 | 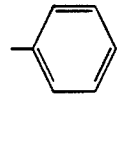 | H | H | 208° C. |
| 22 | 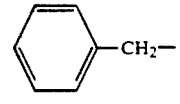 | 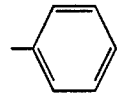 | H | —CH₃ | 146° C. |
| 23 | 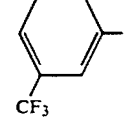 | 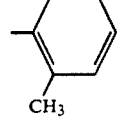 | H | —CH₃ | 148° C. |
| 24 | 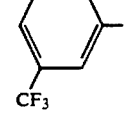 | 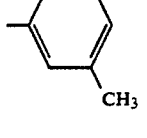 | H | —CH₃ | 64–67° C. |
| 25 | 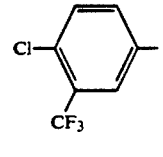 | 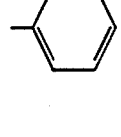 | H | —CH₃ | 62–64° C. |
| 26 | 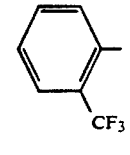 | 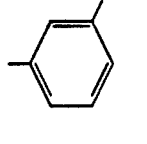 | H | —CH₃ | 95–97° C. |

TABLE 2-continued
| Example No. | R¹ | R² | R³ | R⁴ | Melting point or refractive index |
|---|---|---|---|---|---|
| 27 | 4-CF₃-C₆H₄- 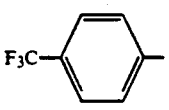 | 3-CF₃-C₆H₄- 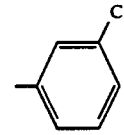 | H | —CH₃ | 148–149° C. |
| 28 | 2,6-(CH₃)₂-C₆H₃- 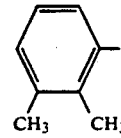 | 3-CF₃-C₆H₄- 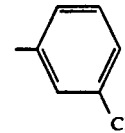 | H | CH₃ | 74° C. |
| 29 | C₂H₅— | 3-CF₃-C₆H₄- 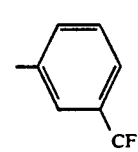 | H | CH₃ | 144–149° C. |
| 30 | n-C₃H₇— | 3-CF₃-C₆H₄- 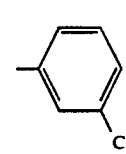 | H | CH₃ | 94–97° C. |
| 31 | n-C₄H₉— | 3-CF₃-C₆H₄- 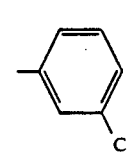 | H | CH₃ | $n_D^{20} = 1.5467$ |
| 32 | 3-CF₃-C₆H₄- 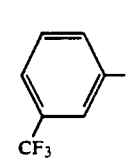 | 4-F-C₆H₄- 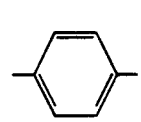 | H | CH₃ | 158° C. |
| 33 | 2-CH₃-C₆H₄- 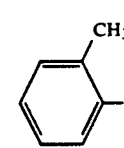 | 3-CF₃-C₆H₄- 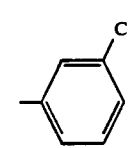 | H | CH₃ | 91–93° C. |
| 34 | 4-Cl-3-CF₃-C₆H₃- 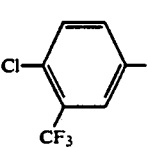 | 4-F-C₆H₄- 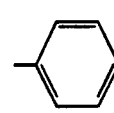 | H | CH₃ | 74–75° C. |
| 35 | 4-Cl-3-CF₃-C₆H₃- 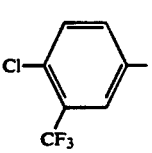 | 4-OCF₃-C₆H₄- 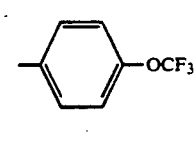 | H | CH₃ | 64–65° C. |
| 36 | 3-CHF₂-C₆H₄- 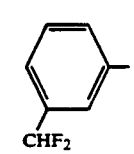 | 3-CF₃-C₆H₄- 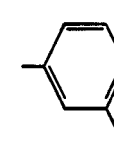 | H | CH₃ | 45–47° C. |

TABLE 2-continued

| Example No. | R¹ | R² | R³ | R⁴ | Melting point or refractive index |
|---|---|---|---|---|---|
| 37 | CH₂=CH—CH₂—CH₂ | 3-CF₃-C₆H₄— | H | CH₃ | 61–62° C. |
| 38 | 3,4-Cl₂-C₆H₃— | 3-CF₃-C₆H₄— | H | CH₃ | 51–52° C. |
| 39 | Cl₂C=CH—CH₂—CH₂— (CCl₂=CH-CH(H)-CH₂-) | 3-CF₃-C₆H₄— | H | CH₃ | $n_D^{20} = 1.5236$ |
| 40 | 4-Cl-3-CF₃-C₆H₃— | 3-CF₃-C₆H₄— | H | CH₃ | 75–76° C. |
| 41 | C₆H₅—CH(CH₃)— | 3-CF₃-C₆H₄— | H | CH₃ | amorphous |
| 42 | 3-CF₃-C₆H₄— | 3-CF₃-C₆H₄— | CH₃ | CH₃ | 110–111° C. |
| 43 | 3-CF₃-C₆H₄— | 3-CF₃-C₆H₄— | H | —CH₂—CH₂—OCH₃ | $n_D^{20} = 1.5278$ |
| 44 | 3-CF₃-C₆H₄— | 3-CF₃-C₆H₄— | H | n-C₃H₇ | 95–96° C. |
| 45 | 3-CF₃-C₆H₄— | 3-CF₃-C₆H₄— | CH₃ | —NH₂ | 88° C. |
| 46 | C₆H₅—CH₂— | 3-CF₃-C₆H₄— | CH₃ | —COCH₃ | amorphous |

TABLE 2-continued
| Example No. | R¹ | R² | R³ | R⁴ | Melting point or refractive index |
|---|---|---|---|---|---|
| 47 | 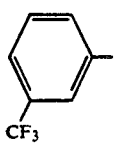 3-CF₃-C₆H₄- | 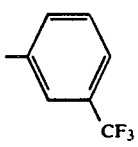 3-CF₃-C₆H₄- | H | H | 68–70° C. |
| 48 | 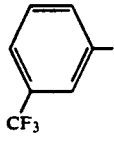 3-CF₃-C₆H₄- | 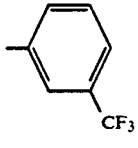 3-CF₃-C₆H₄- | H | —OCH₃ | 42–45° C. |
| 49 | 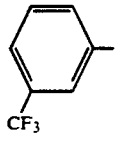 3-CF₃-C₆H₄- | 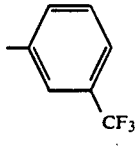 3-CF₃-C₆H₄- | CH₃ | —OH | viscous oil |
| 50 | 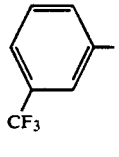 3-CF₃-C₆H₄- | 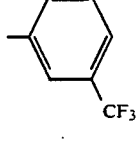 3-CF₃-C₆H₄- | CH₃ | —COCF₃ | 122° C. |
| 51 | 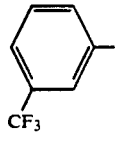 3-CF₃-C₆H₄- | 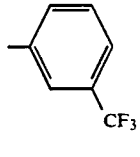 3-CF₃-C₆H₄- | H | —COCH₃ | 178–180° C. |
| 52 | 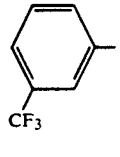 3-CF₃-C₆H₄- | 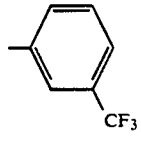 3-CF₃-C₆H₄- | —COCH₃ | —COCH₃ | 174° C. |
| 53 | 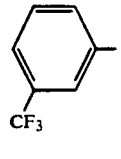 3-CF₃-C₆H₄- | 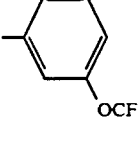 3-OCF₃-C₆H₄- | H | —CH₃ | 47–51° C. |
| 54 | CH₂=C(CH₃)—CH₂— | 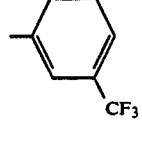 3-CF₃-C₆H₄- | H | —CH₃ | 92° C. |
| 55 | 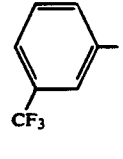 3-CF₃-C₆H₄- | 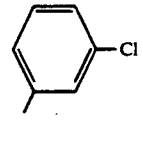 3-Cl-C₆H₄- | H | —CH₃ | viscous oil |
| 56 | 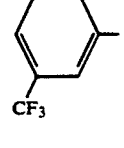 3-CF₃-C₆H₄- | 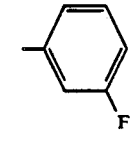 3-F-C₆H₄- | H | —CH₃ | 68–70° C. |

TABLE 2-continued

| Example No. | R¹ | R² | R³ | R⁴ | Melting point or refractive index |
|---|---|---|---|---|---|
| 57 | 3-CH₃-C₆H₄- | 3-CF₃-C₆H₄- | H | —CH₃ | 35-38° C. |
| 58 | Cl—CH=CH—CH₂— | 3-CF₃-C₆H₄- | H | —CH₃ | viscous oil |
| 59 | cyclopentyl-CH₂— | 3-CF₃-C₆H₄- | H | —CH₃ | viscous oil |
| 60 | CH₂=CF—CH₂— | 3-CF₃-C₆H₄- | H | —CH₃ | viscous oil |
| 61 | 3-CF₃-C₆H₄- | 3-CH₃-C₆H₄- | —CH₃ | —COCH₃ | 148° C. |
| 62 | 3-CF₃-C₆H₄- | 3-CH₃-C₆H₄- | —CH₃ | —COCF₃ | 132° C. |
| 63 | n-C₃H₇ | 3-CH₃-C₆H₄- | —CH₃ | —COCF₃ | viscous oil |
| 64 | CH₂=CH—CH₂— | 3-CF₃-C₆H₄- | —CH₃ | —COCF₃ | viscous oil |
| 65 | 3-F-C₆H₄- | 3-CF₃-C₆H₄- | H | CH₃ | 46° C. |
| 66 | 3-Cl-C₆H₄- | 3-CF₃-C₆H₄- | H | CH₃ | 80° C. |

TABLE 2-continued

| Example No. | R¹ | R² | R³ | R⁴ | Melting point or refractive index |
|---|---|---|---|---|---|
| 67 | 3-CH₃-C₆H₄- | 3-CF₃-C₆H₄- | CH₃ | NH₂ | 123° C. |
| 68 | 3-F-C₆H₄- | 3-CF₃-C₆H₄- | CH₃ | NH₂ | 104° C. |
| 69 | 3-Cl-C₆H₄- | 3-CF₃-C₆H₄- | CH₃ | NH₂ | 82° C. |
| 70 | 2,6-(CH₃)₂-C₆H₃- | 3-CF₃-C₆H₄- | CH₃ | NH₂ | 95° C. |

The compound shown in Table 2 as Example 39 can be prepared, for example, as follows:

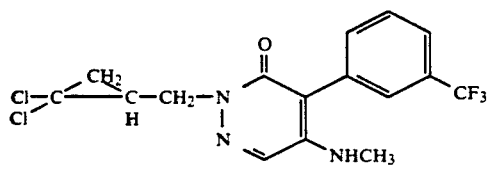

To a Grignard solution, prepared from 1 g (0.04 mol) of magnesium and 9 g (0.04 mol) of 3-trifluoromethyl-bromobenzene in 80 ml of diethyl ether, there are added dropwise 100 ml of absolute toluene, the mixture is warmed to 60° C. and a solution of 5.8 g (0.02 mol) of 2-[1,1-dichlorocyclopropyl-2-methyl]-4,5-dichloro-2H-pyridazin-3-one, dissolved in 100 ml of absolute toluene, is then added dropwise and the reaction mixture is stirred at 60° C. for 3 hours. The mixture is subsequently hydrolysed with a mixture of ice and 1N hydrochloric acid. The ether phase is separated off, washed with water, dried over sodium sulphate and evaporated. The remaining syrup is used for further reaction without further purification.

The crude product from the Grignard reaction is dissolved in 50 ml of ethanol, 10 g (0.1 mol) of a 30% strength solution of methylamine in water are added and the mixture is heated under reflux for 16 hours. The reaction mixture is then concentrated, the residue is taken up with methylene chloride/water, and the organic phase is dried over sodium sulphate and evaporated. After chromatography of the residue on silica gel 60 using methylene chloride/methanol (80:1), 3.4 g (43% of theory) of 2-[1,1-dichlorocyclopropyl-2-methyl]-4-[3-trifluoromethylphenyl]-5-methylamino-2H-pyridazin-3-one of refractive index n_D^20: 1.5236 are obtained.

The compound shown in Table 2 as Example 50 can be prepared, for example, as follows:

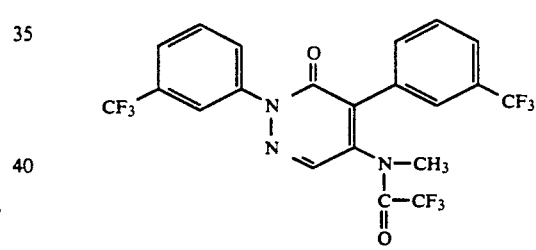

To a solution of 4.1 g (0.01 mol) of 2,4-di-[3-trifluoromethylphenyl]-5-methylamino-2H-pyridazin-3-one in 50 ml of pyridine, there are added dropwise at 10° C. 4.2 g (0.02 mol) of trifluoroacetic anhydride and the mixture is then stirred at room temperature for 16 hours. The reaction mixture is diluted with methylene chloride and extracted with water and three times with 2N hydrochloric acid. The organic phase is dried with sodium sulphate and evaporated. After chromatography of the residue on silica gel 60 using methylene chloride, 3.5 g (68% of theory) of 2,4-di-[3-trifluoromethylphenyl]-5-[trifluoroacetyl-methylamino]-2H-pyridazin-3-one of melting point 122° C. are obtained.

The compound shown in Table 2 as Example 47 can be prepared, for example, as follows:

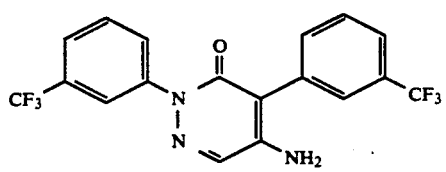

A mixture of 21.9 g (0.05 mol) of 2,4-di-[3-tri-fluoromethylphenyl]-5-chloro-2H-pyridazin-3-one and 100 ml of ethanol is reacted in the presence of excess ammonia (1 mol) in an autoclave at 150° C. for 6 hours. The reaction mixture is evaporated and the residue is chromatographed on silica gel 60 using methylene chloride.

18 g (90% of theory) of 2,4-di-[3-trifluoromethylphenyl]-5-amino-2H-pyridazin-3-one of melting point 68°-70° C. are obtained.

The compound shown in Table 2 as Example 52 can be prepared, for example, as follows:

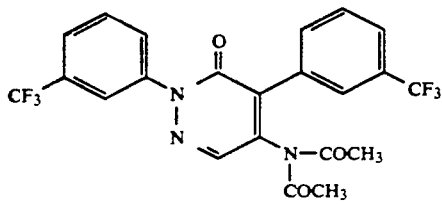

To a solution of 4 g (0.01 mol) of 2,4-di-[3-trifluoromethylphenyl]-5-amino-2H-pyridazin-3-one in 50 ml of dioxane, 0.62 g (0.02 mol) of NaH (80% dispersion) is added and the mixture is warmed to 40° C. for 30 minutes. It is then cooled, 1.6 g (0.02 mol) of acetyl chloride dissolved in 30 ml of dioxane are added dropwise at 15°-20° C. and the mixture is then stirred at room temperature for 16 h. The reaction mixture is diluted with 300 ml of water and extracted twice with 150 ml of methylene chloride. The organic phase is washed with bicarbonate solution and water, dried over sodium sulphate and evaporated. The residue is chromatographed on silica gel 60 using methylene chloride and yields 2.3 g (47% of theory) of 2,4-di-[3-trifluoromethylphenyl]-5-diacetylamino-2H-pyridazin-3-one of melting point 174° C.

The compound shown in Table 2 as Example 45 can be prepared, for example, as follows:

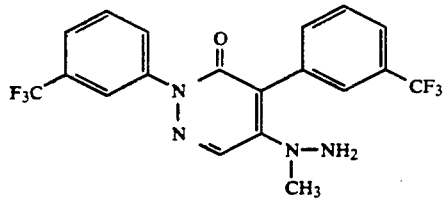

A mixture of 4.2 g (0.01 mol) of 2,4-di-[3-trifluoromethylphenyl]-5-chloro-2H-pyridazin-3-one, 1 g (0.02 mol) of methyl hydrazine and 100 ml of ethanol is heated under reflux for 16 hours. It is then evaporated, the residue is taken up in methylene chloride, the solution is washed with water, and the organic phase is dried over sodium sulphate and evaporated.

After chromatography of the residue on silica gel 60 using methylene chloride, 9.5 g (81% of theory) of 2,4-di-[3-trifluoromethylphenyl]-5-[α-methylhydrazinyl]-2H-pyridazin-3-one are obtained of melting point 88° C.

PREPARATION OF THE STARTING COMPOUNDS

Example (IIa)-1

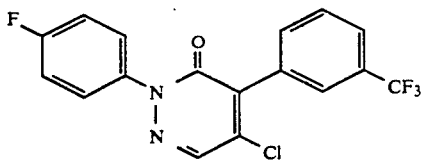

To a Grignard solution, prepared from 1 g (0.04 mol) of magnesium and 9 g (0.04 mol) of 3-trifluoromethyl-bromobenzene in 80 ml of diethyl ether, there is added dropwise at room temperature a solution of 5.2 g (0.02 mol) of 2-[4-fluorophenyl]-4,5-dichloro-2H-pyridazin-3-one in 120 ml of diethyl ether, and the reaction mixture is refluxed for 16 hours. The mixture is subsequently hydrolyzed using a mixture of ice and 1N hydrochloric acid. The ether phase is separated off, washed with water, dried over sodium sulphate and concentrated.

Separation by chromatography on silica gel 60 with methylene chloride as the mobile phase gives 1.8 g (24% of theory) of 2-[4-fluorophenyl]-4-[3-trifluoromethylphenyl]-5-chloro-2H-pyridazin-3-one of melting point 88°-90° C.

The following compounds of the general formula (IIa) are obtained in a corresponding manner and following the general instructions

| Ex. No. | $R^{1-1}$ | $R^{2-1}$ | X | Physical data |
|---|---|---|---|---|
| (IIa)-2 | —CH₃ | ![3-CF₃-phenyl] | Cl | 75° C. |
| (IIa)-3 | ![3-CF₃-phenyl] | ![phenyl] | Cl | 61-63° C. |
| (IIa)-4 | ![benzyl CH₂—] | ![phenyl] | Cl | 54-56° C. |
| (IIa)-5 | —CH₃ | ![phenyl] | Cl | $n_D^{20} = 1.5945$ |
| (IIa)-6 | ![phenyl] | ![3-CF₃-phenyl] | Cl | 54-57° C. |

USE EXAMPLE

In the following Use Example, the compound listed below was employed as comparison substance,

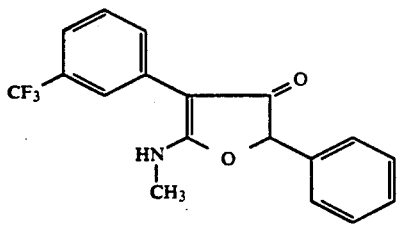
(A)

5-(methylamino)-2-phenyl-4-[3-(trifluoromethyl)-phenyl]-2H-furan-3-one (DE-OS (German Published Specification) 3,422,346).

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added, and the concentrate is diluted with water to the desired concentration.

Seeds of the test plant are sown in normal soil and, after 24 hours, watered with the preparation of active compound. It is expedient here to keep constant the amount of water per unit area. The concentration of active compound in the preparation is of no importance, only the amount of active compound applied per unit area being decisive. After three weeks, the degree of damage to the plants is rated in % of damage compared with the development of the untreated control. The figures denote:

0% = no action (like untreated control)
100% = total destruction

In this test, for example, the compounds of Preparation Examples 1, 6, 7, 9, 16, 24, 26, 29, 30, 31, 32, 33, 36, 49, 53, 55 and 56 show a strong action against weeds, while being tolerated well by crop plants such as, for example, wheat, barley, soya and cotton.

EXAMPLE B

Post-emergence test

Solvent: 5 parts by weight of acetone
Emulsifier: 1 part by weight of alkylaryl polyglycol ether
Wetting agent: 0.1% (relative to the ready-for-use active compound preparation) of a polyoxyethylene 6 tridecyl ether (designated "Renex-36"; CAS 24 938-91-8).

To produce a suitable preparation of active compound, 1 part by weight of active compound is mixed with the stated amount of solvent, the stated amount of emulsifier is added and the concentrate is diluted with water with the addition of the wetting agent to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 1,000 ml of water/ha. After three weeks, the degree of damage to the plants is rated in % damage in comparison to the development of the untreated control. The figures denote:

0% = no action (like untreated control)
100% = total destruction

In this test, for example, the compounds of Preparation Examples 9, 24, 36, 38, 39, 40, 49, 53, 55 and 56 show a strong action against weeds, while being tolerated well by crop plants such as, for example, wheat, barley, soya and cotton.

EXAMPLE C

Defoliation and desiccation of the leaves of cotton

Solvent: 30 parts by weight of dimethylformamide
Emulsifier: 1 part by weight of polyoxyethylene sobitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th true leaf has unfolded completely. In this stage, the plants are sprayed with the preparations of active compound until dripping wet. After 1 week, the shedding of leaves and the desiccation of the leaves are rated, in comparison with the control plants.

In this test, for example, the compound of Preparation Example 1 shows strong plant growth-regulating action.

It will be appreciated that the instant specification is set forth by way of illustration and not limitation, and that various modifications and changes may be made without departing from the spirit and scope of the present invention.

We claim:

1. A 2H-pyridazinone of the formula

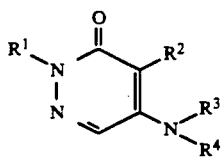
(I)

in which $R^1$ represents methyl, ethyl, n- or i-propyl, n-, i-, s- or t-butyl, methoxymethyl, ethoxymethyl, methoxyethyl or ethoxyethyl, methylthiomethyl, ethylthiomethyl, methylthioethyl, ethylthioethyl, aminomethyl, aminoethyl, methylaminomethyl, methylaminoethyl, dimethylaminomethyl, dimethylaminoethyl, ethylaminomethyl, ethylaminoethyl, diethylaminomethyl, diethylaminoethyl, hydroxymethyl, hydroxyethyl, halogenomethyl having 1–3 fluorine and/or chlorine atoms, halogenoethyl, n- or i-halogenopropyl, n- or i-halogenobutyl, cyanomethyl, cyanoethyl, ally, n- or i-butenyl, n- or i-pentenyl, 2-2-chloropropen-3-yl, 1-chloropropen-3-yl, 1,1-dichloropropen-3-yl, 1,2-dichloropropen-3-yl, 1,1,2-trichloropropen-3-yl, represents methoxycarbonylmethyl, methoxycarbonylethyl, ethoxycarbonylmethyl, or represents cyclopentyl, cyclohexyl, cyclopropylmethyl, cyclopentylmethyl, cyclopentylethyl, cyclohexylmethyl or cyclohexylethyl, each of which is optionally monosubstituted to tetrasubstituted in the cycloalkyl moiety by identical or different substituents selected from the group consisting of fluorine, chlorine, bromine, methyl and ethyl; R¹ furthermore represents phenyl which is optionally monosubstituted or disubstituted by identical or different substituents selected from the group consisting of fluorine, chlorine, bromine, cyano, nitro, methyl, ethyl, n- or i-propyl, n-, i, s- or t-butyl, methoxy, ethoxy, trifluoromethyl, difluoromethyl and trifluoromethoxy;

R² represents phenyl which is optionally monosubstituted or disubstituted by identical or different substituents selected from the group consisting of fluorine, chlorine, bromine, cyano, nitro, methyl, ethyl, n- or i-propyl, n-, i-, s- or t-butyl, methoxy, ethoxy, trifluoromethyl, difluoromethyl and trifluoromethoxy;

R³ represents hydrogen, methyl, ethyl, n- or i-propyl, or represents acetyl, formyl, propionyl, trifluoroacetyl, trichloroacetyl or chloroacetyl, and R⁴ represents hydrogen, hydroxyl, amino, methoxy, ethoxy, methylamino, ethylamino, dimethylamino, diethylamino, methyl, ethyl, n- or i-propyl, methoxycarbonyl, ethoxycarbonyl, methoxycarbonylcarbonyl, ethoxycarbonylcarbonyl, formyl, acetyl, propionyl, difluoroacetyl, trifluoroacetyl, chloroacetyl, dichloroacetyl or trichloroacetyl.

2. A 2H-pyridazinone according to claim 1, in which R¹ represents methyl, ethyl, n- or i-propyl, n-, i-, s- or t-butyl, allyl, n- or i-butenyl, 2-chloropropen-3-yl, 1-chloropropen-3-yl, 1,1-dichloropropen-3-yl, 1,2-dichloropropen-3-yl, 1,1,2-trichloropropen-3-yl, cyclopropylmethyl, 1,1-dichlorocyclopropylmethyl, 1,1-dimethylcyclopropylmethyl, 1,1-dimethyl-2,2-dichlorocyclopropylmethyl, or represents cyclopentyl or cyclohexyl, each of which is optionally monosubstituted or disubstituted by methyl and/or ethyl, or represents phenyl which is optionally monosubstituted or disubstituted by identical or different substituents selected from the group consisting of fluorine, chlorine, bromine, methyl, ethyl, methoxy, ethoxy, trifluoromethyl and trifluoromethoxy;

R² represents phenyl which is monosubstituted or disubstituted by substituents selected from the group consisting of fluorine, chlorine, bromine, methyl, ethyl, methoxy, ethoxy, trifluoromethyl and trifluoromethoxy, R³ represents hydrogen, acetyl or trifluoroacetyl, and R⁴ represents hydroxyl, amino, methylamino, dimethylamino, methyl, acetyl or trifluoroacetyl.

3. A 2H-5-chloro-pyridazinone of the formula

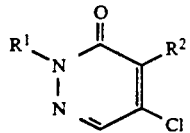

in which

R¹ represents methyl, ethyl, n- or i-propyl, n-, i-, s- or t-butyl, methoxymethyl, ethoxymethyl, methoxyethyl or ethoxyethyl, methylthiomethyl, ethylthiomethyl, methylthioethyl, ethylthioethyl, aminomethyl, aminoethyl, methylaminomethyl, methylaminoethyl, dimethylaminomethyl, dimethylaminoethyl, ethylaminomethyl, ethylaminoethyl, diethylaminomethyl, diethylaminoethyl, hydroxymethyl, hydroxyethyl, halogenomethyl having 1-3 fluorine and/or chlorine atoms, halogenoethyl, n- or i-halogenopropyl, n- or i-halogenobutyl, cyanomethyl, cyanoethyl, allyl, n- or i-butenyl, n- or i-pentenyl, 2-2-chloropropen-3-yl, 1-chloropropen-3-yl, 1,1-dichloropropen-3-yl, 1,2-dichloropropen-3-yl, 1,1,2-trichloropropen-3-yl, represents methoxycarbonylmethyl, methoxycarbonylethyl, ethoxycarbonylmethyl, or represents cyclopentyl, cyclohexyl, cyclopropylmethyl, cyclopentylmethyl, cyclopentylethyl, cyclohexylmethyl or cyclohexylethyl, each of which is optionally monosubstituted to tetrasubstituted in the cycloalkyl moiety by identical or different substituents selected from the group consisting of fluorine, chlorine, bromine, methyl and ethyl; R¹ furthermore represents phenyl which is optionally monosubstituted or disubstituted by identical or different substituents selected from the group consisting of fluorine, chlorine, bromine, cyano, nitro, methyl, ethyl, n- or i-propyl, n-, i-, s- or t-butyl, methoxy, ethoxy, trifluoromethyl, difluoromethyl and trifluoromethoxy; and R² represents phenyl which is optionally monosubstituted or disubstituted by identical or different substituents selected from the group consisting of fluorine, chlorine, bromine, cyano, nitro, methyl, ethyl, n- or i-propyl, n-, i-, s- or t-butyl, methoxy, ethoxy, trifluoromethyl, difluoromethyl and trifluoromethoxy.

4. A compound according to claim 18, wherein such compound is 2-(3-trifluoromethyl-phenyl)-3-(3-chlorophenyl)-5-methylamino-2H-pyridazin-3-one of the formula

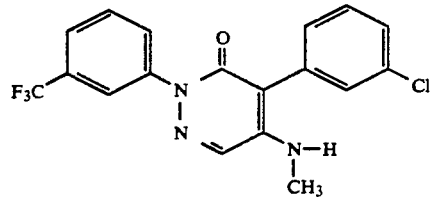

* * * * *

UNITED STATES PATENT AND TRADEMARK OFFICE
CERTIFICATE OF CORRECTION

PATENT NO. : 5,097,028

DATED : March 17, 1992

INVENTOR(S) : Weissmuller et al.

It is certified that error appears in the above-identified patent and that said Letters Patent is hereby corrected as shown below:

Col. 58, line 61    Delete " ally " and substitute -- allyl --

Col. 60, claim 4 line 1    Delete " claim 18 " and substitute -- claim 1 --

Signed and Sealed this

First Day of February, 1994

Attest:

BRUCE LEHMAN

*Attesting Officer*    *Commissioner of Patents and Trademarks*